US009757516B2

(12) United States Patent
Calasso

(10) Patent No.: US 9,757,516 B2
(45) Date of Patent: Sep. 12, 2017

(54) SYSTEM FOR MEDICAL TREATMENT

(71) Applicant: Irio Giuseppe Calasso, Arth (CH)

(72) Inventor: Irio Giuseppe Calasso, Arth (CH)

(73) Assignee: MEDIRIO S.A., Visp (CH)

( * ) Notice: Subject to any disclaimer, the term of this patent is extended or adjusted under 35 U.S.C. 154(b) by 768 days.

(21) Appl. No.: 14/168,599

(22) Filed: Jan. 30, 2014

(65) Prior Publication Data
US 2014/0221914 A1 Aug. 7, 2014

(30) Foreign Application Priority Data

Feb. 6, 2013 (EP) ..................................... 13154302

(51) Int. Cl.
*A61M 5/145* (2006.01)
*A61M 5/168* (2006.01)
*A61M 5/14* (2006.01)
*A61M 5/142* (2006.01)

(52) U.S. Cl.
CPC ........ *A61M 5/16813* (2013.01); *A61M 5/141* (2013.01); *A61M 5/1413* (2013.01);
(Continued)

(58) Field of Classification Search
CPC .......... A61M 5/14276; A61M 5/14526; A61M 5/16877; A61M 2205/332; A61M 2205/3317; A61M 2205/3523; A61M 2205/3592; A61M 2205/3569; H04B 5/0037
See application file for complete search history.

(56) References Cited

U.S. PATENT DOCUMENTS 4,593,703 A * 6/1986 Cosman ............... A61B 5/0002
600/438
5,569,187 A * 10/1996 Kaiser ............... A61M 5/14276
604/67

(Continued)

FOREIGN PATENT DOCUMENTS

EP 2022518 A1 2/2009
EP 2055228 B1 5/2009
WO WO2005/039674 A1 5/2005

*Primary Examiner* — Matthew F Desanto
(74) *Attorney, Agent, or Firm* — Robert E. Alderson, Jr.

(57) ABSTRACT

A medical device and a system for medical treatment comprising the medical device are disclosed. The medical device comprises a fluidic conduit and/or is configured to be operatively coupled to a fluidic conduit. The medical device comprises a flow regulator for regulating the flow of a fluid in the fluidic conduit and at least two movable elements, which are passively displaceable as a function of a fluidic pressure change in the fluidic conduit or actively displaceable for regulating the flow of fluid in the fluidic conduit. The medical device further comprises at least one transponder circuit comprising at least one transponder element chosen from a capacitor, an inductor, a resistor, or combinations thereof, being arranged with respect to the movable elements such that the transponder circuit has a capacitance or inductance or resistance or resonant frequency or Q factor, which changes as a function of the displacement of the movable elements. The system further comprises a control device comprising a transceiver, wherein the transceiver is configured to transmit energy to the transponder circuit and to read out the capacitance and/or the inductance and/or the resistance and/or the resonant frequency and/or the Q factor of the transponder circuit, such as to determine with the same transponder circuit whether there is a displacement of any of the movable elements. A foil comprising at least one transponder circuit to be arranged in the medical device is also disclosed.

16 Claims, 6 Drawing Sheets

(52) U.S. Cl.
CPC .... *A61M 5/14248* (2013.01); *A61M 5/16881* (2013.01); *A61M 5/14232* (2013.01); *A61M 5/14276* (2013.01); *A61M 2205/3317* (2013.01); *A61M 2205/3515* (2013.01); *A61M 2205/3523* (2013.01); *A61M 2205/3569* (2013.01); *A61M 2205/3592* (2013.01); *A61M 2205/502* (2013.01); *A61M 2205/6054* (2013.01); *A61M 2205/8243* (2013.01); *A61M 2209/01* (2013.01)

(56) References Cited

U.S. PATENT DOCUMENTS

| | | | |
|---|---|---|---|
| 5,820,589 A * | 10/1998 | Torgerson | A61M 5/14276 604/93.01 |
| 2005/0092079 A1 * | 5/2005 | Ales | F16K 7/14 73/270 |
| 2011/0152825 A1 * | 6/2011 | Marggi | A61M 5/14526 604/500 |
| 2012/0245515 A1 | 9/2012 | Calasso et al. | |

\* cited by examiner

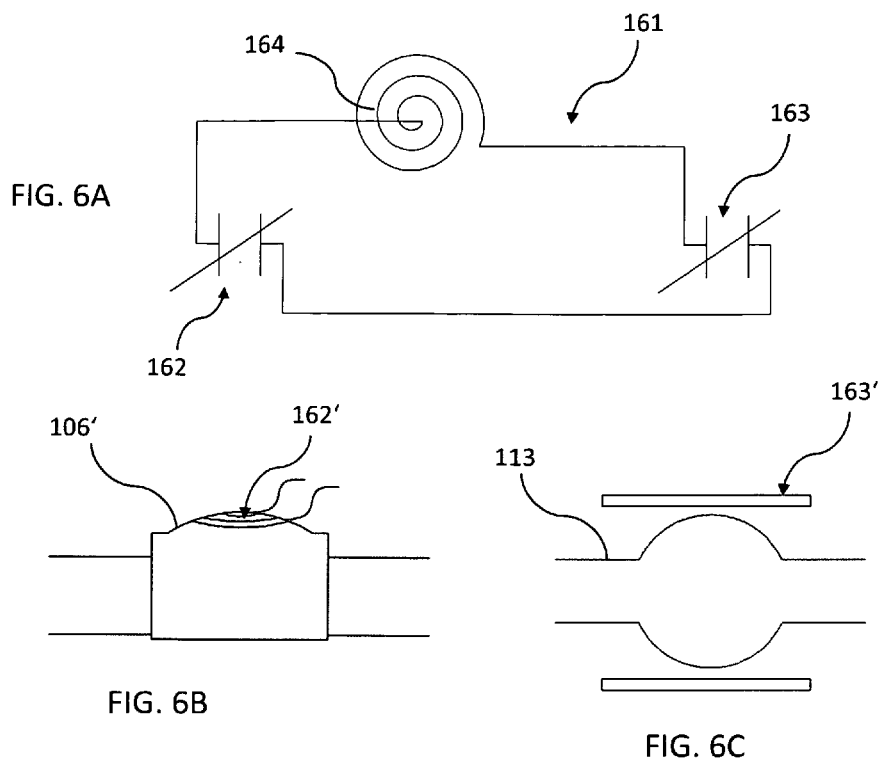
FIG. 6A
FIG. 6B
FIG. 6C
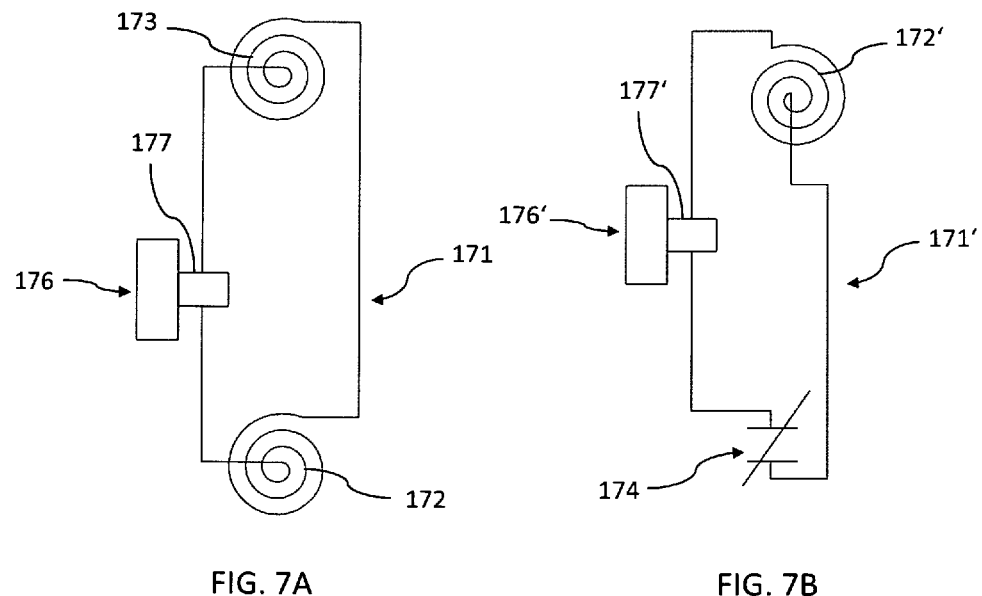
FIG. 7A
FIG. 7B

SYSTEM FOR MEDICAL TREATMENT

FIELD OF THE INVENTION

The present invention relates to a system comprising a medical device for regulating the flow of a fluid for medical treatment and a control device.

BACKGROUND OF THE INVENTION

Some medical conditions require the regular infusion of doses of medicaments as medical treatment. These medicaments are often provided as liquid solutions to be infused, e.g. transdermally. Diabetic patients, for example, may require several infusions of insulin every day. Patients with chronic diseases may require frequent doses of a pain drug, etc . . . In the attempt to make the life of these patients easier, infusion devices have been developed. The infusion devices known in the art typically comprise a syringe, and use electro-mechanical pumping to deliver the medicament to the patient via tubing through the skin. They typically comprise also all the elements needed for operation and control, e.g. a processor, electric components, a battery, buttons or switches located on the housing of the device, visual feedback via text or graphic screen, such as an LCD, etc . . . These are however expensive, difficult to use and tend to be bulky and uncomfortable. Moreover, they require specialized care, maintenance and cleaning to assure proper functionality and safety for their intended long-term use. Other types of infusion devices have been therefore proposed, which employ a disposable medical device comprising a medicament reservoir to be placed in contact with a patient and a reusable control device for controlling the operation of the disposable medical device, such as disclosed in US 2012245515 A1. The advantage of such a system is that the disposable medical device comprises a minimum number of components and is therefore small and cheap. Moreover, it is comfortable, discreet and easy to use. In addition, it is safe to use since it can be activated and controlled in a specific manner via the control device, wherein the control device is also an energy source for the medical device. US 2012245515 A1 further discloses that the control device may advantageously comprise a feedback system, e.g. a receiver, capable of receiving information from the delivery device, e.g. a signal confirming that the correct amount and form of energy has been transferred and/or that the correct dose of medicament has been delivered and/or that an atypical situation has been encountered, e.g. a clogging or when the reservoir is empty. The feedback signal may be for example, electromagnetic, e.g. generated by the movement of magnets or by a coil in the delivery device. US 2012245515 A1 further discloses that an RFID chip may also be integrated in the disposable medical device, which may be configured to send a feedback signal, e.g. when the reservoir is empty, for example by being contacted directly or indirectly by a movable element.

US 20110152825 A1 discloses an administering device for administering a fluid product through the use of pressure, the device being modular, including a base unit and a cartridge, wherein the base unit contains driving components and the cartridge is configured to be detachably connected to the base unit. The cartridge has a fluid reservoir and a pressure monitoring device having a pressure sensor and a transfer device operatively coupled to the pressure sensor. The pressure-monitoring device can be activated by an externally applied, alternating electromagnetic field, whereby data can be read, without contact, using the fluid pressure. In one embodiment, the pressure sensor contains a snap disk and the transfer device is an RFID transponder, wherein the base unit comprises a pressure reading device, which is constructed for producing a corresponding alternating electromagnetic field and, depending on the response to the alternating field, for determining a fluid pressure-dependent property of the transfer device.

SUMMARY OF THE INVENTION

It is against the above background that the present invention provides certain unobvious advantages and advancements over the prior art. In particular, a new medical device and a system comprising the medical device and a control device are herein disclosed, the medical device comprising a flow regulator for regulating the flow of a fluid in a fluidic conduit, wherein the system is able to determine in a simple, cost-effective and space-saving manner at least two different conditions of the medical device associated with fluid flow. Moreover the same technical effect may be achieved for different types of flow regulators and for different types of medical devices. In particular, the medical device may comprise a fluidic conduit or be configured to be operatively coupled to a fluidic conduit, and may be configured to be externally placed in contact with a patient or to be implanted. A foil to be arranged in the medical device is also disclosed.

These and other features and advantages will be more fully understood from the following detailed description taken together with the accompanying claims. It is noted that the scope of the claims is defined by the recitations therein and not by the specific discussion of features and advantages set forth in the description.

BRIEF DESCRIPTION OF THE DRAWINGS

FIG. 6A shows schematically another type of transponder circuit configured as a resonator.

FIG. 6B shows schematically one way of configuring the transponder circuit of FIG. 6A.

FIG. 6C shows schematically another way of configuring the transponder circuit of FIG. 6A.

FIG. 7A shows schematically an example of transponder circuit comprising a telemetric tag.

FIG. 7B shows schematically a variant of the transponder circuit of FIG. 7A.

DETAILED DESCRIPTION

Figure 1:
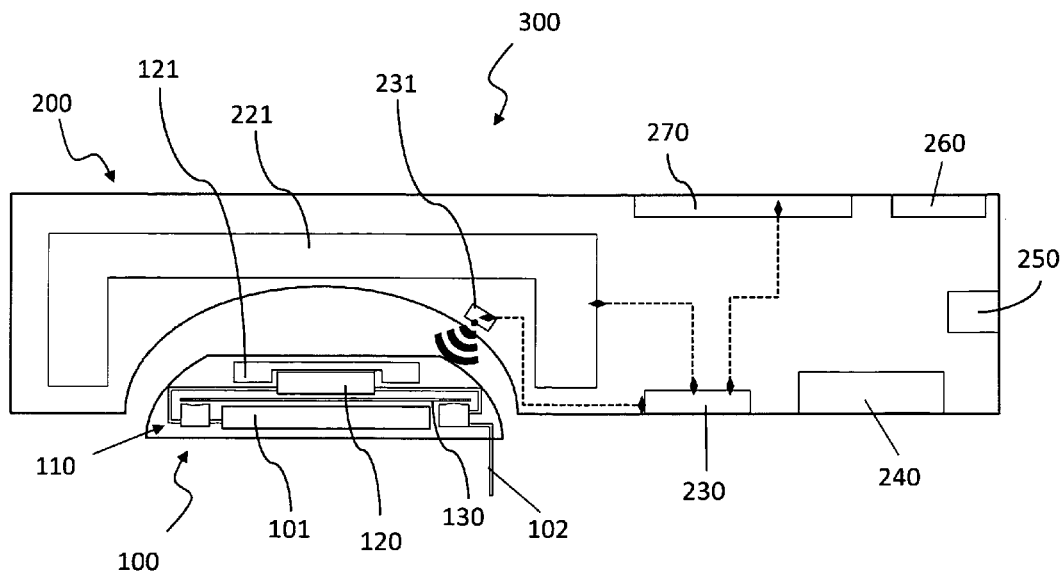
FIG. 1 depicts schematically a system for medical treatment comprising a medical device and a separate hand-held device in energy-transfer position.

A system for medical treatment is herein disclosed. The system comprises a medical device and a control device.

A "medical device" according to the present invention is a device, which is configured to be placed in contact with a patient and to perform medical treatment by regulating the flow of fluid in the patient's body or into the patient's body or out of the patient's body.

"In contact" thus means either in dermal contact with the patient, e.g. removably fixed, e.g. by an adhesive base, to the skin of the patient, or more generally in body contact, comprising the inside of the body, such as fixed at least in part in a cavity of the body or implanted inside the body.

The medical device comprises a fluidic conduit and/or is configured to be operatively coupled to a fluidic conduit, the medical device further comprising a flow regulator for regulating the flow of a fluid in the fluidic conduit for medical treatment.

The term "fluidic conduit" is herein used to indicate any sort of fluid containing structure for transporting fluid and/or storing and/or receiving fluid. It may be made of metal or polymer or composite material, made of one piece or more pieces directly or indirectly connected to each other. The fluidic conduit is not limited to any particular geometry or form and may comprise parts having different cross-sections, such as e.g. a part with a tubular or substantially cylindrical cross-section and a part with a substantially rectangular cross-section. In particular, the fluidic conduit may be embodied as a tubing, a fluidic vessel or channel, and may comprise a chamber, a reservoir, an infusion element, etc . . .

"Configured to be operatively coupled to a fluidic conduit" means that the fluidic conduit is not necessarily part of the medical device or not completely part of the medical device. The fluidic conduit may be for example a body fluidic duct, such as a blood vessel, lymphatic vessel, cerebrospinal fluid duct, urethral duct, esophagus or intestinal tract and the medical device is configured to be operatively coupled to the fluidic conduit, typically to the outside of the fluidic conduit such as to regulate the fluidic flow though the fluidic conduit when operated, e.g. by restricting from the outside the cross-section of the fluidic conduit. Operative coupling may occur however also by fluidic connection between a fluidic conduit of the medical device and a fluidic conduit external to the medical device, so that passage of fluid through the external fluidic conduit may occur via the fluidic conduit internal to the medical device.

The term "fluid" indicates a medium or a substance in a medium, typically a liquid, capable of flowing through the fluidic conduit and whose flow regulation results in medical treatment. An example of fluid is a medicament for treating a medical condition, e.g. insulin to treat a diabetic condition, a pain-treating drug to treat the symptoms of a chronic disease, an anti-coagulation drug to reduce the risk of thrombosis, e.g. after surgery, a hormone to treat or change other medical conditions, etc . . . The fluid may be however a body fluid or an external fluid passing through a body fluidic conduit.

According to one embodiment the medical device is a medical infusion device configured to deliver trans-dermally or intravenously multiple doses of a fluidic medicament to a patient without the need of multiple injections. A typical example of patient is a diabetic patient requiring frequent doses of insulin, e.g. in correspondence to each meal. According to one embodiment the medical device is an implantable device or a device partly in the body and partly out of the body, e.g. a catheter. The medical device may be embodied as a valve device configured to enable/disable fluid flow or vary the flow rate of a fluid, e.g. a body fluid, or as a continuous infusion device, configured to deliver a continuous flow of a medicament with a flow rate, which may be changed over time. Medical treatment may otherwise result from regulation of the flow of a fluid from outside the body into the body or from inside the body to the external of the body, e.g. to temporarily interrupt the flow of a fluid, e.g. urine in incontinent patients, or to drain off excess of a fluid produced by the body, e.g. interstitial fluid in edematous patients, or from regulation of the flow of a body fluid within the body, i.e. from one part of the body to another, e.g. cerebrospinal fluid in order to decrease intracranial pressure, or from regulation of the passage of an external fluid through the body, e.g. food or drinks through the digestive duct, e.g. in order to regulate appetite and treat obesity.

A "flow regulator" is an apparatus configured to regulate, i.e. to change by increasing, decreasing, interrupting or resuming the flow of a fluid through the fluidic conduit. This may comprise pumping a fluid through the fluidic conduit, either continuously or at intervals, either at constant or variable flow rate.

According to one embodiment, the flow regulator is arranged or is configured to be arranged between an inlet side and an outlet side of the fluidic conduit such as to regulate the flow of a fluid from the inlet side to the outlet side.

According to some embodiments the inlet side comprises or is fluidically connected to a reservoir and the outlet side comprises or is fluidically connected to an infusion element.

The reservoir may be configured for holding a volume of a medicament to be delivered which is sufficient for several doses. In particular, the medical device may be disposable or semi disposable and thus at least in part intended to be replaced after a period of time, e.g. 1 to 7 days, typically 2 to 4 days, after several doses of the medicament have been infused, e.g. when the medicament is exhausted or the reservoir is nearly empty. The reservoir may be any type of container with any shape, suitable to contain a medicament of choice. The reservoir, thus preferably comprises a chemical- and/or bio-compatible material inert to the medicament to be contained. According to certain embodiments the reservoir is pre-loaded with the medicament in the manufacturing process. The reservoir may thus be suitable for storing a medicament within the device for a long period of time, e.g. several months or years before the device is used. According to certain embodiments the reservoir is configured to be loaded with the medicament by the user, i.e. the patient or care giver, before use. According to certain embodiments the reservoir is configured to be loaded into or onto the device before use, either before or after loading the reservoir with the medicament.

According to certain embodiments the reservoir is a collapsible pouch, configured to expand from a collapsed status to an expanded status upon loading the reservoir with the medicament and from an expanded status to a collapsed status upon emptying the reservoir, e.g. upon pumping the medicament.

The infusion element may be configured for the trans-dermal infusion of the medicament, i.e. configured to remain in a trans-dermal position for the duration of use of the medical device such as to allow infusion of a dose of medicament from the medical device into the body when requested. The infusion element may comprise a thin needle insertable at a controlled depth, a cannula, a catheter, or other form of hollow fluid transport conduit, insertable e.g. via a removable needle, and configured to infuse a medicament. The infusion element may comprise or be made of metal such as steel, of a ceramic material, of a silica-based material, of a polymeric material such silicone or Teflon, or any composite thereof. The infusion element may comprise one or more outlets, e.g. a plurality of micro-needles, configured to penetrate the skin and/or infuse the medicament in parallel or sequentially. The infusion element may comprise a triggering element, comprising e.g. a resilient element, e.g. a spring, configured to trigger skin penetration.

According to some embodiments the flow regulator is either a pump for pumping the fluid through the fluidic conduit or a valve or flow restrictor operatively coupled or coupable to the fluidic conduit for regulating the flow of a fluid in the fluidic conduit.

A "pump" may be any sort of pumping mechanism, e.g. a peristaltic pump, a membrane pump, an electro-osmotic pump, a micropump, as known in the art, and configured for pumping the fluid through the fluidic conduit. A "valve" may be any sort of valve having at least one valve inlet and at least one valve outlet for interrupting, resuming, diverting, decreasing or increasing the flow of a fluid passing through the fluidic conduit via the valve. Thus the valve typically comprises at least one passage for the fluid, which is fluidically connected to the fluidic conduit, and which can be opened or closed or opened to a different extent for regulating the amount of fluid passing per time unit through the valve, i.e. the flow rate. A "flow restrictor" is a device similar in function to a valve but different with respect to the way it is coupled or coupable to the fluidic conduit. In particular, the flow restrictor is configured to regulate the flow rate of a fluid in the fluidic conduit by restricting the fluidic conduit, e.g. to a different extent, from the outside. An example of flow restrictor is a push or pull or tightening element configured to apply a pressure to the fluidic conduit thereby deforming the fluidic conduit and obstructing or reducing passage of fluid through the fluidic conduit when pushed or pulled or tightened. Another example of flow restrictor is a clamp or a loop arranged around the fluidic conduit and configured to restrict the cross-section of the fluidic conduit when pulled. Closing the loop to different extents may result in different flow rates or full obstruction. The actions of both the valve and the flow restrictor may be reversible and repeatable as necessary for medical treatment.

The medical device further comprises at least two movable elements, which are passively displaceable as a function of a fluidic pressure change in the fluidic conduit or actively displaceable for regulating the flow of fluid in the fluidic conduit. A "passively displaceable element" is either a part of the fluid conduit, which is movable, e.g. flexible, expandable and/or contractible, as a result of an increase or decrease respectively of fluidic pressure in the fluidic conduit, or an element externally coupled to the fluidic conduit, such as to be directly or indirectly movable as a result of the displacement of at least part of the fluidic conduit when the fluidic pressure inside the fluidic conduit changes. According to one embodiment the fluidic conduit is a hollow tubing made of elastomeric flexible material such as silicone. The tubing itself may be flexible, expandable or contractible as a result of an increase or decrease respectively of fluidic pressure in the tubing. According to one embodiment the fluidic conduit comprises at least one membrane, wherein the membrane is the passively displaceable element. An "actively displaceable element" is an element coupled to the fluidic conduit, the displacement of which causes a change in fluidic pressure in the fluidic conduit. An example of actively displaceable element is regulator movable element such as a valve element or flow restrictor element, the displacement of which actively causes a change in fluidic pressure, e.g. an increase in pressure due to restriction or obstruction of the fluidic flow.

The medical device further comprises at least one transponder circuit comprising at least one transponder element chosen from a capacitor (C), an inductor (L), a resistor (R), or combinations thereof, being arranged with respect to the movable elements such that the transponder circuit has a capacitance or inductance or resistance, or resonant frequency or Q factor in case the transponder circuit is a resonator, which changes as a function of the displacement of the movable elements. According to a preferred embodiment the transponder circuit is "passive" in the sense that it is configured to obtain energy required for its function (activating energy) from an external field only, e.g. in the form of electromagnetic energy such as a radio frequency signals or magnetic oscillation, from outside the medical device, and is thus designed to operate without its own permanent source of energy.

In particular, the same transponder circuit comprises at least one L and/or C and/or R transponder element arranged with respect to each movable element or with respect to at least two movable elements such that displacement of any of said movable elements can be determined with the same circuit. An advantage of such a transponder circuit is that space and cost savings can be achieved. The medical device can be therefore simpler, smaller and cost effective. According to some embodiments the transponder circuit is also in contactless relationship with the movable elements and therefore easy to integrate in the medical device. The "transponder circuit" is thus a movement sensor element of the medical device, which is preferably passive and is configured to detect movement of at least two movable elements as above defined. In order to increase sensitivity of detection the movable elements may be made of or comprise a magnetically or electrically susceptible material, e.g. a metal, which may be in the form of a coating, paint or pattern.

According to one embodiment, the medical device comprises an inlet movable element and an outlet movable element coupled to an inlet/outlet transponder element. The same (inlet/outlet) transponder element may thus be coupled to two movable elements to detect movement of any of the two inlet and outlet movable elements respectively. This may be achieved if the inlet and outlet movable elements and/or the inlet side and outlet side of the fluidic conduit are arranged close to each other, e.g. adjacent to each other. Analogously, according to another embodiment, the medical device comprises at least two regulator movable elements coupled to at least one transponder element. The same regulator transponder element may thus be coupled to two regulator movable elements to detect movement of any of the two regulator movable elements respectively.

According to one embodiment, the medical device comprises at least two of the following: an inlet movable element coupled to an inlet transponder element at the inlet side, an outlet movable element coupled to an outlet transponder element at the outlet side, a regulator movable element coupled to a regulator transponder element. Here "coupled" means that a transponder element is placed in proximity to or in contact with the respective movable element such that the capacitance or inductance or resistance or resonant frequency or Q factor of the transponder circuit is influenced by the movable element when it is displaced. According to one embodiment, the transponder circuit comprises an inlet inductor and an outlet inductor connected in series to a capacitor.

According to some embodiments, the transponder circuit is integrated in a foil or plate like substrate arranged in the medical device such that a transponder element is coupled with a respective movable element. According to some embodiments the foil or plate like substrate comprises one or more transponder circuits, each transponder circuit comprising at least one transponder element coupled to a movable element.

The foil or plate like substrate is preferably made of plastics or other electrically insulating material. The transponder circuit may be printed on the substrate and/or sandwiched between two layers of substrate. The two layers may be joined by any conventional technique, such as adhesive, thermal bonding, etc . . .

According to some embodiments, the movable elements are of different type or size and/or are displaceable to a different extent and/or arranged with respect to the transponder elements such as to change the capacitance and/or the inductance and/or the resistance and/or the resonant frequency and/or the Q factor of the transponder circuit to a different extent or in an inverse manner when displaced.

According to some embodiments, the transponder elements are of different type or size and/or are arranged with respect to the movable elements such that the capacitance and/or the inductance and/or the resistance and/or the resonant frequency and/or the Q factor of the transponder circuit is changed to a different extent or in an inverse manner when the movable elements are displaced.

The system further comprises a control device. A "control device" is a device configured to communicate with the medical device, thereby controlling the operation of the medical device. In particular, the control device comprises a transceiver, wherein the transceiver is configured to transmit energy to the transponder circuit of the medical device and to read out the capacitance and/or the inductance and/or the resistance and/or the resonant frequency and/or the Q factor of the transponder circuit, such as to determine with the same transponder circuit whether there is a displacement of any of the movable elements.

In general terms, the term "transceiver" means an apparatus acting both as a transmitter and as a receiver and the function of which at least comprising the act of generating a sampling (activating) field and receiving signals emitted by the transponder circuit as a response thereto.

According to some embodiments, to ensure high data security, it may be advantageous in the present context to encrypt the transferred data.

According to a preferred embodiment the flow regulator comprises a passive energy-receiving unit and the control device comprises an energy-transfer unit for transferring operational energy to the energy-receiving unit for operating the flow regulator, and thereby regulating the flow of fluid through the fluidic conduit for performing medical treatment.

Transferring operational energy to the energy-receiving unit may comprise unlocking one or more safe-lock mechanisms and may comprise transferring rotational force to at least one rotor and/or axial force to at least one axial element of the energy-receiving unit. The safe lock mechanism is intended to prevent uncontrolled operation of the medical device. Transferring operational energy to the energy-receiving unit may comprise providing power to the medical device, e.g. by induction or magnetic coupling. The energy to be received by the energy-receiving unit comes from the energy-transfer unit of the control device, typically without an energy source being present in the medical device itself. The medical device may however comprise an internal energy source, e.g. an auxiliary energy source.

According to some embodiments, the medical device further comprises a telemetric tag connected to the transponder circuit. In particular, the transceiver is configured to transmit energy to the telemetric tag, which may comprise an auxiliary circuit, for measuring the capacitance and/or the inductance and/or the resistance and/or the resonant frequency and/or the Q factor of the transponder circuit and to read out the capacitance and/or the inductance and/or the resistance and/or the resonant frequency and/or the Q factor of the transponder circuit via the telemetric tag. An example of telemetric tag is a Radio-Frequency-Identification (RFID) tag or near field communication (NFC) tag. The telemetric tag may be further configured to store information related to the medical device such that the medical device may be identified by the control device. According to one embodiment the telemetric tag stores information related to the fluidic conduit such as the diameter, length, which may be variable for different medical devices due to manufacturing tolerances. The telemetric tag may further or in alternative store information related to the pump such as the specifications of the pump and/or related to the reservoir such as the reservoir capacity and/or type of medicament. The control device may then be configured to read out said information via the transceiver and to operate the flow regulator based on said information. In this way, the medical device may be calibrated therefore achieving higher precision in the regulation of the fluid flow.

According to some embodiments, the control device comprises a logic unit. A "logic unit" is a computing unit, embodied e.g. as a programmable logic controller running a computer-readable program provided with instructions to perform operations to determine one or more conditions or events associated with the medical device and/or to react in response to one or more conditions or events. In particular, the logic unit is configured to discriminate which one or more of the movable elements are displaced based on the read out of the capacitance and/or the inductance and/or the resistance and/or the resonant frequency and/or the Q factor of the transponder circuit. This may comprise comparing the read out data with stored reference data and/or reference data measured before operation of the flow regulator, and to identify from this comparison if there is a change or deviation. The control device may comprise a plurality of logic units independent from each other e.g. dedicated to particular tasks or in communication with each other, e.g. cooperating with each other.

According to some embodiments, the logic unit is configured to determine any one or more of the following conditions.

According to one condition, the fluidic pressure remains substantially unchanged during operation of the flow regulator. This condition indicates normal or correct operation of the medical device when the flow regulator is a pump, which pumps a fluid in operation. The term "substantially unchanged" means that the average fluidic pressure in the fluidic conduit remains unchanged during operation. In practice, the fluidic pressure may locally change during pumping, e.g. at the inlet side and at the outlet side, e.g. in a periodic manner. This may be the case when using certain types of pumps, for example a peristaltic or membrane pump, by which the fluid may advance in a pulsing manner. This in turn may cause a periodic displacement of the movable elements during operation, which is however normal and may be monitored via the transponder circuit to confirm correct operation. Also, at the outlet side, a slight increase of the fluidic pressure may occur due to a possible restriction of the fluidic conduit at the infusion element, and/or due to flow resistance when the fluid enters the body.

According to another condition, a persistent decrease of fluidic pressure occurs at the inlet side of the fluidic conduit, when compared to the fluidic pressure during normal operation, which is typically caused by exhaustion of fluid at the inlet side, e.g. when the reservoir is empty. This is determined as a persistent displacement of a passively displaceable inlet movable element.

According to another condition a persistent increase of fluidic pressure occurs at the inlet side, when compared to the fluidic pressure during normal operation, which is typically caused by excess of fluid at the inlet side. This is determined as a persistent displacement of a passively displaceable inlet movable element, wherein the direction of displacement is typically opposite to that occurring in case of a decrease in fluidic pressure.

According to another condition a persistent increase of fluidic pressure occurs at the outlet side, when compared to the fluidic pressure during normal operation, which is typically caused by an occlusion or partial occlusion at the outlet side, which blocks or significantly reduced the fluid flow. This is determined as a persistent displacement of a passively displaceable outlet movable element.

Also, in case the flow regulator is e.g. a valve or flow restrictor, the operational status of the flow regulator may be determined by determining the position of the actively displaceable elements or flow regulator elements. In case the flow regulator is a pump, e.g. a peristaltic or membrane pump, the operational status of the flow regulator may be determined by monitoring a periodic displacement of the movable elements during operation.

According to another condition, passage of fluid in the fluidic conduit for the first time, e.g. when priming the medical device, may be determined by determining the displacement of any of the movable elements, thereby confirming proper priming.

The term "persistent" or "persistently" is herein used to indicate a prolonged period of time, i.e. longer than it may occur during normal operation, e.g. for at least the duration of operation of the flow regulator. According to some embodiments, the control device is configured to operate or to interrupt operation of the flow regulator in response to a determined condition, and/or to generate a user identifiable signal.

The control device may be configured to be removably attached to the medical device, e.g. for the duration of use of the medical device, wherein the medical device may be disposable and the control device may be reusable.

According to a preferred embodiment, the control device is configured to be temporarily placed in an energy-transfer position with respect to the medical device for operating the flow regulator and/or for transferring energy to the transponder circuit, wherein in the energy-transfer position the control device is separated from the medical device. In particular, the control device may be configured as a hand-held device to be temporarily hand-held in the energy-transfer position.

The system may further comprise a positioning sensor to verify the position of the medical device and to ensure optimal energy transfer between the control device and the medical device.

The control device may be used as an interface device enabling the user, e.g. the patient and/or a technician/doctor/care giver to interact with the medical device, for example to set the amount of a medicament dose, to verify that the conditions for delivery of such dose are satisfied, and to alert the user should any atypical situation occur in the procedure or to react to an atypical situation, by suggesting or executing a remedy operation.

Thus all or most electronic components, such as e.g. a processor, a memory, switch and operational buttons, electric circuits, printed circuit board, wires, a visual and/or Braille-like display, a battery or other form of power supply, one or more ports for recharging and/or for connecting to other devices, e.g. a computer, e.g. for exchanging data, e.g. wirelessly, alert or warning signal emitters, are integrated in the control device rather than in the medical device.

The medical device thus remains simple, small and low-cost, and may be disposable or implantable. The control device may have additional functions. It may be for example configured as a body parameter meter, e.g. as a glucose meter, e.g. to monitor the response to the medical treatment. It may comprise even functions such as a telephone, a gps, etc . . . The control device may be a common interface device for several medical devices of the same or different types and/or for different patients.

More in detail the present invention is explained with reference to the drawings representing schematically exemplary embodiments.

Figure 2:
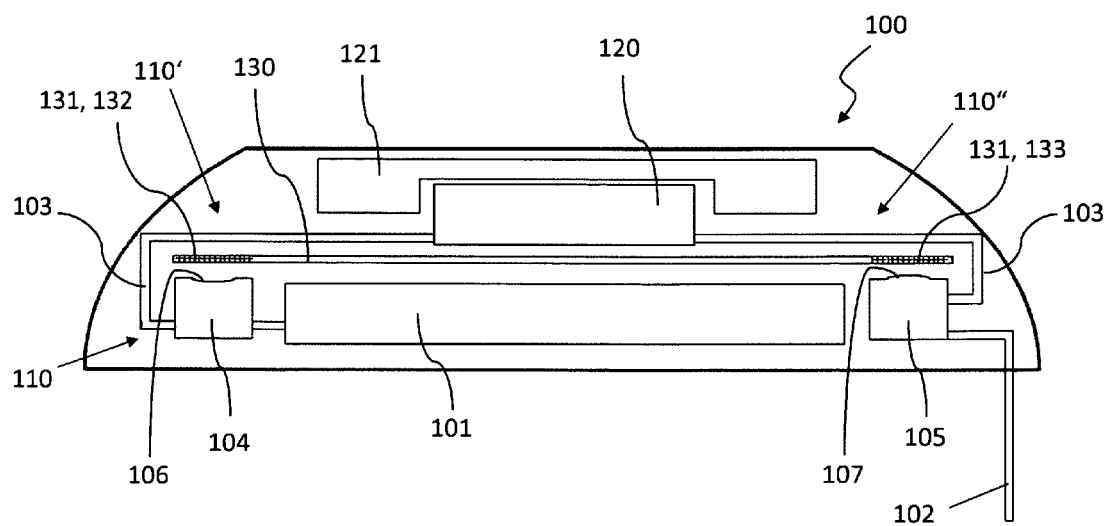
FIG. 2 is a magnification of the medical device of FIG. 1.

FIG. 1 depicts schematically and not to scale a system 300 for medical treatment, in this case for the trans-dermal delivery of doses of a medicament. The system 300 comprises a medical device 100 and a control device 200 configured as a separate hand-held device. The medical device 100 and the control device 200 are shown in an energy transfer-position. FIG. 2 is a magnification of the medical device 100. The medical device 100 comprises a reservoir 101 for holding a medicament to be delivered, a trans-dermal infusion element 102 for delivering doses of the medicament and a fluidic conduit 110 for transporting the medicament from the reservoir 101 to the infusion element 102. The reservoir 101 is a collapsible pouch. The medical device 100 further comprises a flow regulator 120. The flow regulator 120 comprises a passive energy-receiving unit 121 configured to receive operational energy from the control device 200 when the control device 200 is in the energy-transfer position and to transfer the received energy to the flow regulator 120. The flow regulator 120 transforms then the energy received from the energy-receiving unit 121 into pumping force for pumping doses of the medicament from the reservoir 101 to the trans-dermal infusion element 102. The control device 200 thereby operates the flow regulator 120 via the energy-receiving unit 121. In particular, the flow regulator 120 is a peristaltic pump operatively coupled to the tubing 103 such as to pump medicament through the fluidic conduit 110 when operated.

The fluidic conduit 110 comprises an inlet side 110' and an outlet side 110" and the flow regulator 120 is arranged between the inlet side 110' and the outlet side 110" such as to pump the medicament from the inlet side 110' to the outlet side 110' when operated. The fluidic conduit 110 comprises a tubing 103, wherein the tubing 103 is operatively coupled to the flow regulator 120 such that operation of the flow regulator 120 results in peristaltic pumping of medicament through the fluidic conduit 110. The fluidic conduit 110 comprises an inlet chamber 104 fluidically connected to the tubing 103 at the inlet side 110' and an outlet chamber 105 fluidically connected to the tubing 103 at the outlet side 110". The inlet chamber 104 comprises an inlet movable element 106 and the outlet chamber 105 comprises an outlet movable element 107, wherein the inlet movable element 106 and the outlet movable element 107 are passively displaceable as a function of a fluidic pressure change in the fluidic conduit 110. In particular, the inlet movable element 106 and the outlet movable element 107 are fluid-tight membranes sealing an opening of the inlet chamber 104 and outlet chamber 105 respectively. The membranes 106, 107 have elastic properties and are therefore displaceable, in this case stretchable or deformable as a function of a fluidic pressure change in the inlet chamber 104 and outlet chamber 105 respectively. The medical device 100 further comprises a transponder circuit 131 integrated in an electrically insulating foil-like substrate 130. The transponder circuit 131 is a passive circuit configured to obtain energy from an external field provided by the control device 200. The transponder circuit 131 comprises an inlet transponder element 132, an inlet inductor, and an outlet transponder element 133, an outlet inductor. The transponder circuit 131 further comprises a capacitor (not shown) connected in series to the inlet inductor 132 and outlet inductor 133 such as to form a resonator. In particular, the transponder circuit 131 is arranged in the foil 130 and the foil 130 is arranged in the medical device 100 at a distance from the membranes 106, 107 such that the inlet inductor 132 is contactless coupled to the membrane 106 and the outlet inductor 133 is contactless coupled to the membrane 107. In such a way, the transponder circuit 130 has a resonant frequency, which changes as a function of the displacement of the movable elements 106, 107.

The control device 200 comprises a transceiver 231, wherein the transceiver is configured to transmit energy to the transponder circuit 131 and to read out the resonant frequency of the transponder circuit 131, such as to determine with the same transponder circuit 131 whether there is a displacement of any of the membranes 106, 107. The membranes 106, 107 may comprise a magnetically or electrically susceptible material, e.g. a metal (not shown) in order to increase sensitivity of detection of the displacement by the transponder circuit 131.

The control device 200 further comprises an energy-transfer unit 221 for transferring operational energy to the energy-receiving unit 121 of the medical device 100 for operating the peristaltic pump 120. In particular, the energy-receiving unit 121 is embodied as a rotor engaged with a plurality of peristaltic wheels (not shown), the rotor comprising one or more ferromagnetic elements. The energy-transfer unit 221 is embodied as a drive rotor connected to a motor (not shown), the drive rotor comprising a plurality of magnets, configured to establish a magnetic coupling with the ferromagnetic elements of the energy-receiving unit 121. The energy-transfer unit 221 thus provides rotational force to the peristaltic pump 120 via the energy-receiving unit 121 when the energy-receiving unit 121 and the energy-transfer unit 221 are in the energy-transfer position and magnetic coupling is established.

The control device 200 further comprises a logic unit 230 configured to discriminate which membrane 106, 107 is displaced based on the read out of the resonant frequency of the transponder circuit 131 by the transceiver 231, and based on that to determine any one or more conditions, which may occur during operation of the medical device 100.

The control device 200 further comprises among other elements, a battery 240, a port 250 for recharging and for connecting to other devices, buttons 260 for operating the control device 200, a display 270. The logic unit 230 is in this example in electric communication with at least the transceiver 231, the energy-transfer unit 221 and the display 270. In particular, the logic unit 230 is configured to operate or to interrupt operation of the energy-transfer unit 221 and therefore of the flow regulator in response to a determined condition, and to generate a user identifiable signal. The control device 200 is therefore an interface device enabling the user, e.g. the patient and/or a technician/doctor/care giver to interact with the medical device 100, for example to set the amount of a medicament dose, to verify that the conditions for delivery of such dose are satisfied, and to alert the user should any atypical situation occur in the procedure or to react to an atypical situation, by suggesting or executing a remedy operation.

FIG. 3A to FIG. 3F depict schematically some of the conditions, which may occur during operation of the medical device 100 of FIG. 2. For clarity reasons, only those components of the medical device 100, which are relevant for understanding, are schematically shown and further simplified. In particular, FIG. 3A-3F show the flow regulator (pump) 120 arranged between the inlet side 110' and the outlet side 110" of the fluidic conduit 110, the inlet side 110' comprising the inlet chamber 104 with inlet membrane 106 and the outlet side 110" comprising the outlet chamber 105 with outlet membrane 107. FIG. 3A-3D also show the foil 130, with the transponder circuit 131 separated for clarity and schematically represented above the foil 130. FIG. 3E shows a different embodiment with a transponder circuit 131' separated as above from foil 130', which is a variant of the transponder circuit 131. FIG. 3F shows a variant of the embodiment of FIG. 3E. The transponder circuits 131, 131' comprise an inlet inductor 132 contactless coupled to the inlet membrane 106 and an outlet inductor 133, 133' contactless coupled to the outlet membrane 107. The inlet inductor 132 and the outlet inductor 133, 133' are connected in series to a capacitor 134. The transponder circuits 131, 131' are therefore configured as passive resonators and the transceiver 231 is configured to activate the resonator and to read out the resonant frequency $\omega_0$ before starting operation of the pump 120, e.g. as soon as the control device 200 is placed in the energy-transfer position, and to read out the resonant frequency $\omega$ during and/or after operation of the pump 120, wherein $\omega_0 = 1/\sqrt{(L_0 \times C)}$, that is 1 divided by the square root of (the inductance multiplied by the capacitance) before starting operation of the pump 120 and wherein $\omega = 1/\sqrt{(L \times C)}$, that is 1 divided by the square root of (the inductance multiplied by the capacitance) during and/or after operation of the pump 120. It is preferred to read out the resonance frequency $\omega_0$ also before operation of the pump 120 because this may vary depending on external factors such as the ambient temperature. A relative read out is therefore preferred to an absolute read out.

More in detail, FIG. 3A shows a first operational condition wherein the fluidic pressure in the fluidic conduit 110 remains substantially unchanged during operation of the pump 120. According to this condition the membranes 106, 107 are not displaced or are minimally displaced or are displaced in a predictable manner, typically in an alternating and periodic manner, like pulsing, when the peristaltic pump 120 is operated. In particular, the outlet membrane 107 may undergo a slight positive displacement followed by a relaxation phase and the inlet membrane 106 may undergo a slight negative displacement followed by a relaxation phase. The average resonant frequency $\omega$ is therefore comparable to $\omega_0$ ($\omega$ is about equal to $\omega_0$). By a continuous read out the predictable displacement of the membranes 106, 107 may be monitored to further confirm normal operation. The logic unit 230 determines by this read out and comparison that the medical device 100 operates correctly.

FIG. 3B shows another operational condition, which may occur when e.g. there is an occlusion at the outlet side 110". In this case the fluidic pressure at the outlet side 110" increases when the pump 120 is operated and the outlet membrane 107 is persistently displaced outwards, i.e. undergoes a positive displacement. This displacement causes in turn a change of inductance in the outlet inductor 133 and therefore a change in the resonant frequency $\omega$ of the transponder circuit 131. In this case $\omega < \omega_0$ and the logic unit 230 determines by this read out and comparison that there is an atypical situation at the outlet side 110", e.g. an occlusion.

FIG. 3C shows another operational condition, which may occur when e.g. the reservoir 101 is empty. In this case the fluidic pressure at the inlet side 110' decreases when the pump 120 is operated and the inlet membrane 106 is persistently displaced downwards, i.e. undergoes a negative displacement. This displacement causes in turn a change of inductance in the inlet inductor 132 and therefore a change in the resonant frequency $\omega$ of the transponder circuit 131. In this case $\omega > \omega_0$ and the logic unit 230 determines by this read out and comparison that there is an atypical situation at the inlet side 110', e.g. exhaustion of medicament or empty reservoir. Determining this condition at the inlet side 110' is useful for knowing in advance when the medicament is about to be exhausted, so that medicament exhaustion may not occur for example while a dose of medicament is being delivered and the user is prompted to replace the medical device 100 or the reservoir 101 before the next dose can be delivered. The inlet chamber 104 may be dimensioned such as to contain a sufficient amount of medicament to guarantee at least one last dose after this operational condition has been determined.

FIG. 3D shows another operational condition, which is very unlikely to occur, e.g. when the reservoir 101 is empty and there is also an occlusion at the outlet side 110". In this case the fluidic pressure at the inlet side 110' decreases when the pump 120 is operated and the membrane 107 is persistently displaced downwards, i.e. undergoes a negative displacement. However, the fluidic pressure at the outlet side 110" increases when the pump 120 is operated and the outlet membrane 107 is persistently displaced (stretched) outwards, i.e. undergoes a positive displacement. In such a case, a change in the resonant frequency $\omega$ of the transponder circuit 131 with respect to $\omega_0$ may not be detectable and in some circumstances may be interpreted as a correct operation as shown in FIG. 3A. In order to improve discrimination in similar cases, a transponder circuit 131' with discriminating transponder elements such as an inlet inductor 132 and an outlet inductor 133' with different inductances may be employed, wherein the resonant frequency $\omega$ of the transponder circuit 131' is changed to a different extent by the displacement of the inlet membrane 106 and outlet membrane 107 respectively at parity of displacement ($\omega < \omega_0$ in FIG. 3E). Alternatively or in addition, an inlet membrane 106 and an outlet membrane 107' or other movable elements of different size and/or with different magnetic or electric susceptibility and/or with different arrangement with respect to the movable elements may be employed ($\omega < \omega_0$ in FIG. 3F).

Figure 3:
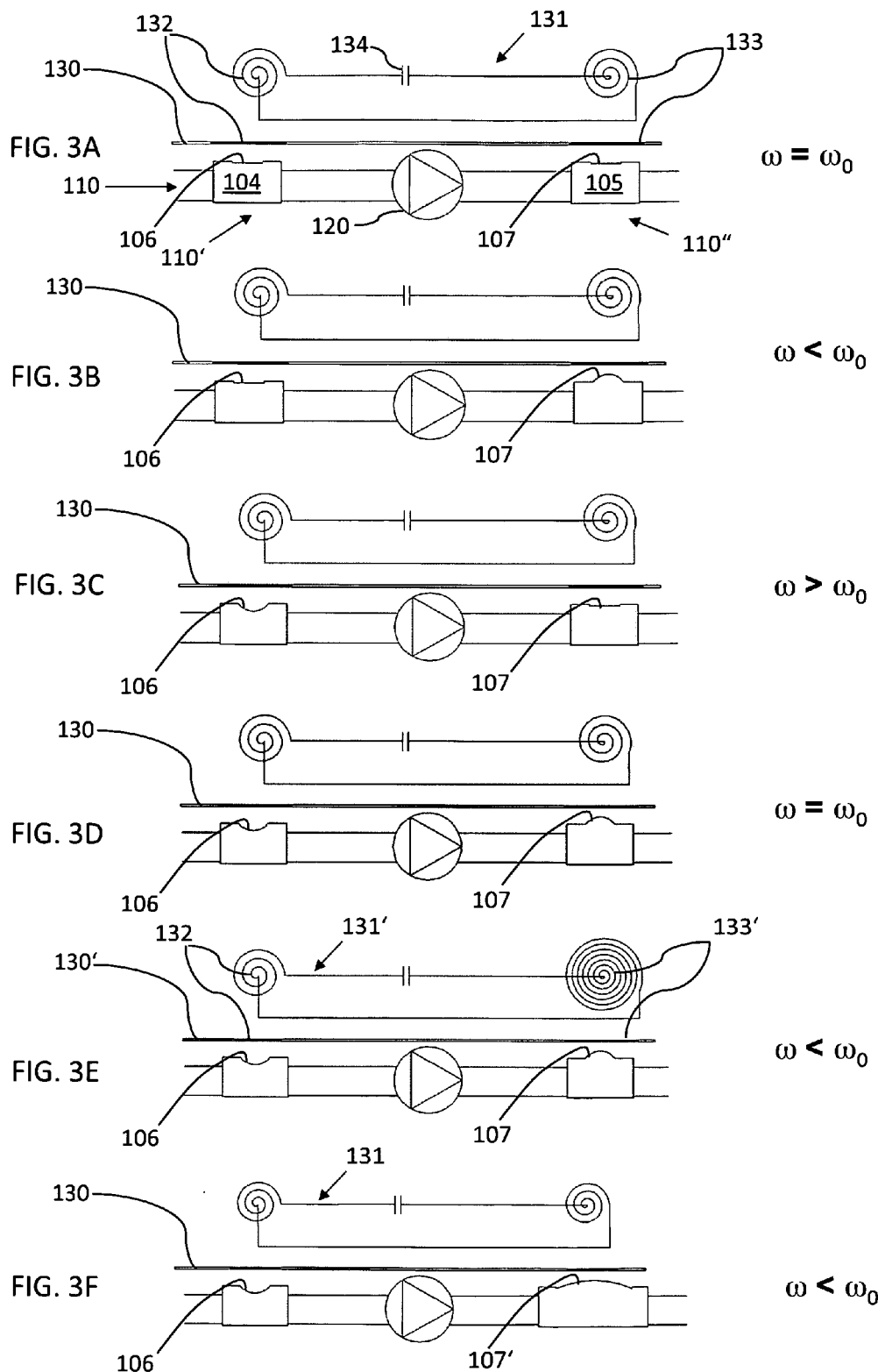
FIG. 3A depicts schematically an operational condition, which may occur during operation of the medical device of FIG. 2.
FIG. 3B depicts schematically another operational condition, which may occur during operation of the medical device of FIG. 2.
FIG. 3C depicts schematically another operational condition, which may occur during operation of the medical device of FIG. 2.
FIG. 3D depicts schematically yet another operational condition, which may occur during operation of the medical device of FIG. 2.
FIG. 3E depicts schematically an embodiment to improve discrimination of the operational condition of FIG. 3D.
FIG. 3F depicts schematically a variant of the embodiment of FIG. 3E.
Figure 4:
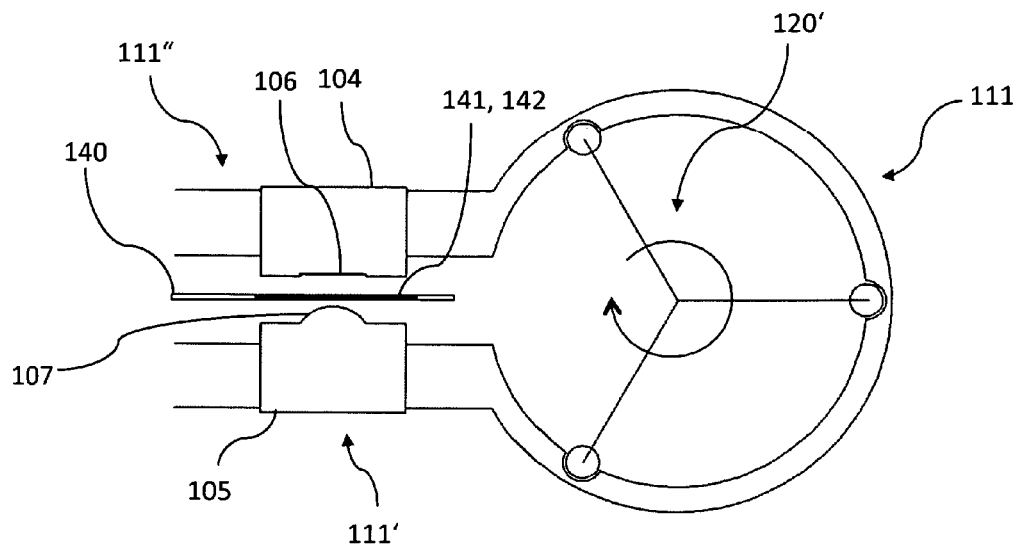
FIG. 4 shows schematically an embodiment comprising a transponder circuit with an inlet/outlet transponder element.

FIG. 4 shows schematically a variant of the embodiments of FIG. 2 and FIG. 3. In particular, FIG. 4 shows a flow regulator 120' embodied as a peristaltic pump arranged between an inlet side 111' and an outlet side 111" of a fluidic conduit 111. The difference with the fluidic conduit 110 of FIGS. 2 and 3 is that the fluidic conduit 111 is arranged around the pump 120' in a way that the inlet side 111' and the outlet side 111" and in particular chambers 104 at the inlet side 111' and chamber 105 at the outlet side 111" are arranged adjacent each other so that inlet membrane 106 at the inlet side 111' is facing outlet membrane 107 at the outlet side 111". A foil 140 with an integrated transponder circuit 141, such as a resonator, is arranged between the inlet membrane 106 and the outlet membrane 107 such that an inlet/outlet transponder element 142, e.g. an inductor (inlet/outlet inductor) is contactless coupled to both the inlet membrane 106 and the outlet membrane 107. Displacement of any of the membranes 106, 107 may thereby be determined with only one transponder element 142. In particular, depending on the direction, extent and duration of the displacement (temporary or persistent) by either one or both of the membranes 106, 107 different operational conditions may be determined analogously to at least some of the embodiments of FIG. 3. With specific reference to FIG. 4, a condition of occlusion at the outlet side 111' is indicated, wherein the outlet membrane 107 undergoes a persistent positive displacement. This is determined as $\omega < \omega_0$.

Figure 5:
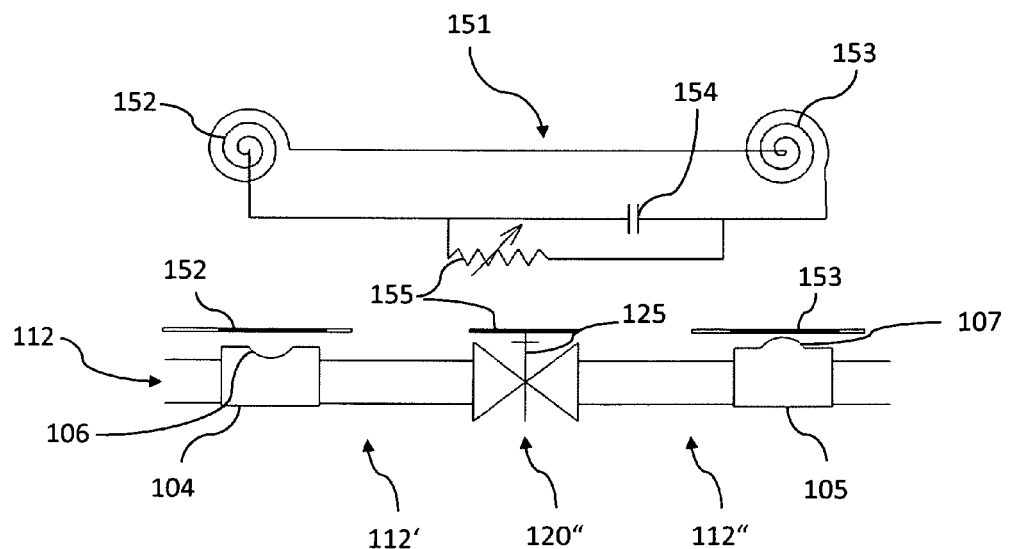
FIG. 5 shows a variant of the embodiment of FIG. 3 with a different type of flow regulator and transponder circuit.

FIG. 5 shows a variant of the embodiment of FIG. 3 with a different type of flow regulator 120" and a different type of transponder circuit 151. In particular, the flow regulator 120" is a valve comprising a fluid passage, which is fluidically connected to an inlet side 112' and an outlet side 112" of a fluidic conduit 112, and which can be opened or closed or opened to a different extent for regulating the amount of fluid passing through the valve 120" by moving a valve regulator element 125. The inlet side 112' comprises an inlet chamber 104 with inlet membrane 106 and the outlet side 112' comprises an outlet chamber 105 with outlet membrane 107. The transponder circuit 151 comprises an inlet inductor 152 and an outlet inductor 153 connected in series to a capacitor 154 and in parallel to a variable resistor 155. In particular, the transponder circuit 151 is arranged with respect to the valve 120" and the fluidic conduit 112 such that the inlet inductor 152 is contactless coupled to the inlet membrane 106, the outlet inductor 153 is contactless coupled to the outlet membrane 107 and the variable resistor 155 is coupled to the valve regulator element 125. The variable resistor 155 is an example of a regulator transponder element coupled to a regulator movable element. By reading out the resonant frequency of the transponder circuit 151 is therefore possible to determine displacement of the membranes 106, 107 thereby determining a fluidic pressure change in the fluidic conduit 112 analogously to the embodiments of FIG. 3. It is however also possible to read out the Q factor of the transponder circuit 151 and thereby to determine the status, e.g. open, closed or intermediate position of the valve 120".

FIG. 6A to FIG. 6C show schematically another type of passive transponder circuit 161 configured as a resonator. In particular, as shown in FIG. 6A, the transponder circuit 161 comprises two variable capacitors 162, 163 connected in series to an inductor 164. A variable capacitor 162, 163 may be configured in different ways. FIG. 6B shows an example of variable capacitor 162' integrated on a membrane 106', wherein displacement of the membrane 106' caused by a fluidic pressure change causes a change of capacitance and therefore a change of resonant frequency ω of the transponder circuit 161. FIG. 6C shows another example of variable capacitor 163' wherein a fluidic conduit 113 is arranged between the plates of the variable capacitor 163'. The plates may be in contact or in contactless relationship with the fluidic conduit 113. Displacement of the fluidic conduit 113 caused by a fluidic pressure change causes a change of capacitance and therefore a change of resonant frequency ω of the transponder circuit 161.

Figure 8:
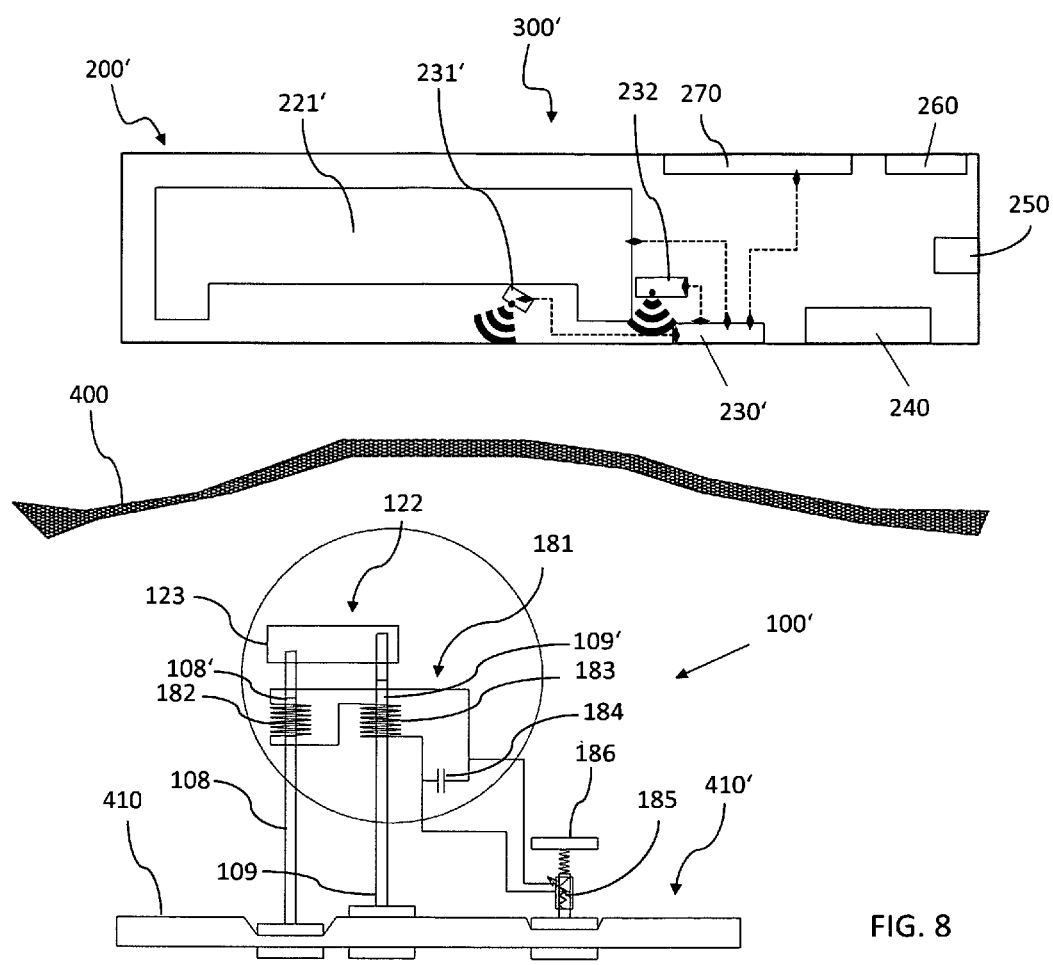
FIG. 8 shows schematically a variant of the system of FIG. 1 comprising a different type of medical device.

FIG. 7A and FIG. 7B show schematically examples of transponder circuits 171, 171' comprising an RFID tag 176, 176'. In particular, FIG. 7A shows a transponder circuit 171 comprising two inductors 172, 173 connected to an RFID tag 176 comprising an auxiliary circuit 177 for measuring the inductance of the transponder circuit 171, wherein the transceiver 231 is configured to transmit energy to the RFID tag 176 for measuring the inductance of the transponder circuit 171 as a function of the displacement of respective movable elements coupled thereto and to read out the inductance of the transponder circuit via the telemetric tag 176. FIG. 7B shows a transponder circuit 171' comprising an inductor 172' and a variable capacitor 174 connected to an RFID tag 176' comprising an auxiliary circuit 177' for measuring the inductance and/or the capacitance of the transponder circuit 171', wherein the transceiver 231 is configured to transmit energy to the RFID tag 176' for measuring the inductance and/or the capacitance of the transponder circuit 171' as a function of the displacement of respective movable elements coupled thereto and to read out the inductance and/or the capacitance of the transponder circuit 171' via the telemetric tag 176'. FIG. 8 shows schematically a system 300', which is a variant of the system 300 of FIG. 1. In particular, the system 300' comprises a different type of medical device 100' and a control device 200' similar to the control device 200 of FIG. 1. The medical device 100' is an implantable device and is depicted schematically implanted under a layer of body tissue 400. In particular, the medical device 100' is shown operatively coupled to a fluidic conduit 410, which in this case is a body fluid duct. The medical device 100' comprises a flow regulator 122 for regulating the flow of a fluid in the fluidic conduit for medical treatment. The flow regulator 122 is a flow restrictor comprising two regulator movable elements 108, 109, which are configured as clamps and are actively displaceable for regulating the flow of fluid in the fluidic conduit 410. The flow regulator 122 further comprises a passive energy-receiving unit 123 configured to receive operational energy from the control device 200' when the control device 200' is in an energy-transfer position. The flow regulator 122 transforms then the energy transferred by the energy-receiving unit 123 into an active displacement of one or both of the two actively displaceable elements 108, 109. In this example, the medical device 100' further comprises a passively displaceable element 186, in this case a resilient clamp, operatively coupled to the fluidic conduit 410 at an inlet side 410', which is displaceable as a function of the fluidic pressure in the fluidic conduit 410. The medical device 100' further comprises a transponder circuit 181 comprising two inductors 182, 183 connected in series to a capacitor 184 and in parallel to a variable resistor 185. The inductors 182, 183 are regulator transponder elements, each arranged with respect to a respective actively displaceable element 108, 109 such that the transponder circuit 181 has a resonant frequency ω, which changes as a function of the displacement of the actively displaceable elements 108, 109. In order to increase sensitivity of detection of the displacement, the actively displaceable elements 108, 109 comprise magnetically susceptible parts 108', 109', which change position with respect to the inductors 182, 183 respectively when the actively displaceable elements 108, 109 move. The variable resistor 185 is arranged with respect to the passively displaceable movable element 186 such that the transponder circuit has a Q factor, which changes as a function of the displacement of the passively displaceable element 186. The transponder circuit 181 is for some aspects similar to the transponder circuit 151 of FIG. 5.

The control device 200' comprises a transceiver 231', wherein the transceiver 231' is configured to transmit energy to the transponder circuit 181 and to read out the resonant frequency ω as well as the Q factor of the transponder circuit 181, such as to determine with the same transponder circuit 181 whether there is a displacement of any of the actively displaceable elements 108, 109 and/or of the passively displaceable element 186.

The control device 200' further comprises a logic unit 230' configured to determine the position of the actively displaceable elements 108, 109 and of the passively displaceable element 186 based on the read out of the resonant frequency ω and the Q factor of the transponder circuit 181 by the transceiver 231', and based on that to determine any one or more conditions, which may occur during operation of the medical device 100' and eventually to react accordingly. To give an example, a possible condition, which may occur is an increase of fluidic pressure at the inlet side 410' indicating excess of fluid at the inlet side 410'. Based on the determination of such a condition the logic unit 230' may then instruct the control device 200' to actively open one or both of the clamps 108, 109, e.g. temporarily, such as to decrease the fluidic pressure in the fluidic conduit 410 by allowing the fluid therein to flow through. It may be advantageous to use at least two actively displaceable elements 108, 109 such as to better control the fluid flow in the fluid conduct or to be able to alternate restriction of the fluidic conduit 410 at different positions thereby avoiding stress of the fluidic conduit 410 always at the same position. Accurate control and/or verification of the displacement of the actively displaceable elements 108, 109 as well as control of the fluidic pressure may be thus achieved with the same transponder circuit 181.

The control device 200' further comprises an energy-transfer unit 221' similar to the energy-transfer unit 221 of system 300, configured to establish magnetic coupling with the energy-receiving unit 123 in the energy-transfer position. Given the fact that the medical device 100' is implanted and therefore not visible, in order to more easily find and/or maintain and/or confirm the energy-transfer position a positioning sensor 232 is also provided in the control device 200'. The logic unit 230' is in this example in electric communication also with the positioning sensor 232. In particular, the logic unit 230' is further configured to operate or to interrupt operation of the energy-transfer unit 221' and therefore of the flow regulator 122 based on the position of the control device 200' with respect to the medical device 100'.The control device 200' further comprises as the control device 200, a battery 240, a port 250 for recharging and for connecting to other devices, buttons 260 for operating the control device 200' and a display 270.

Figure 9:
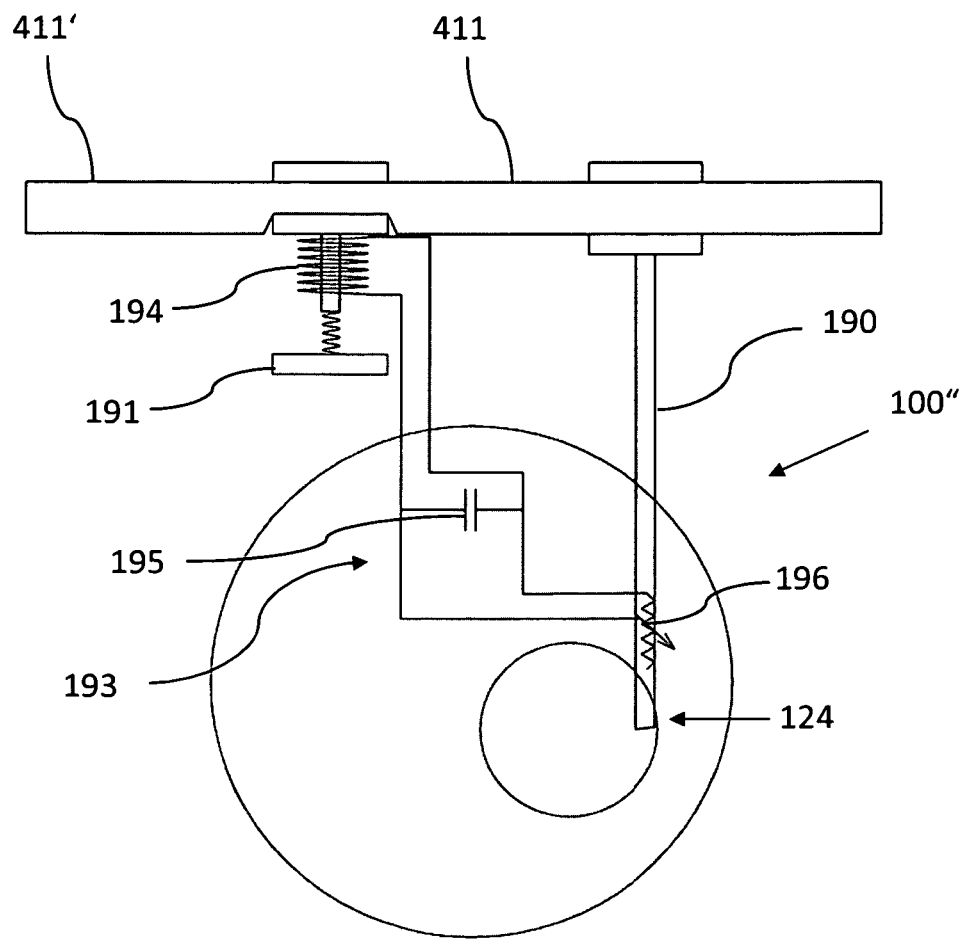
FIG. 9 shows schematically a variant of the medical device of FIG. 8.

FIG. 9 shows schematically a medical device 100", which is a variant of the medical device 100' of FIG. 8. The medical device 100" is also implantable and is depicted schematically operatively coupled to a fluidic conduit 411, which is a body fluid vessel. The medical device 100" further comprises a flow regulator 124 for regulating the flow of a fluid in the fluidic conduit 411 for medical treatment. The flow regulator 124 is a flow restrictor comprising a regulator movable element 190, which is configured as a clamp and is actively displaceable for regulating the flow of fluid in the fluidic conduit 411. The medical device 100" further comprises a passively displaceable element 191, configured as a resilient clamp, operatively coupled to the fluidic conduit 411 at an inlet side 411', which is displaceable as a function of the fluidic pressure in the fluidic conduit 411. The medical device 100" further comprises a transponder circuit 193 comprising an inductor 194 connected in series to a capacitor 195 and in parallel to a variable resistor 196. The variable resistor 196 is a regulator transponder element, arranged with respect to the actively displaceable regulator movable element 190 such that the transponder circuit 193 has a Q factor, which changes as a function of the displacement of the actively displaceable regulator movable element 190. The inductor 194 is arranged with respect to the passively displaceable element 191 such that the transponder circuit 193 has a resonant frequency ω, which changes as a function of the displacement of the passively displaceable element 191. Accurate control and/or verification of the displacement of the actively displaceable regulator movable element 190 as well as control of the fluidic pressure in the fluidic conduit 411 may thus be achieved with the same transponder circuit 193.

Of course numerous variations of the described embodiments are possible without departing from the scope of the invention. It is also noted that terms like "preferably" or "preferred" and "typically" or "typical" or "advantageous" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The invention claimed is:

1. A medical system comprising,
a medical device adapted to be placed on a patient and further comprising
a fluidic conduit configured to deliver a medical treatment to the patient,
a flow regulator for regulating the flow of a fluid in the fluidic conduit for medical treatment,
at least two movable elements, which are displaceable as a function of a fluidic pressure change in the fluidic conduit or actively displaceable, for regulating the flow of fluid in the fluidic conduit;
at least one passive resonant transponder circuit comprising at least one transponder element being arranged with respect to the movable elements such that the transponder circuit has a capacitance or inductance or resistance or resonant frequency or Q factor, which changes as a function of the displacement of the movable elements and is used to determine one or more different operational conditions of the medical device;
and a control device, the control device comprising a transceiver, wherein the transceiver is configured to transmit energy to the passive transponder circuit and to read out the resonant frequency and/or the Q factor of the transponder circuit to determine with the same transponder circuit whether there is a displacement of any of the movable elements.

2. System according to claim 1 wherein the flow regulator is arranged or is configured to be arranged between an inlet side and an outlet side of the fluidic conduit such as to regulate the flow of a fluid from the inlet side to the outlet side.

3. System according to claim 2 wherein the medical device comprises at least two of
an inlet movable element coupled to an inlet transponder element at the inlet side,
an outlet movable element coupled to an outlet transponder element at the outlet side,
a regulator movable element coupled to a regulator transponder element.

4. System according to claim 3 wherein the transponder circuit comprises an inlet inductor and an outlet inductor connected in series to a capacitor.

5. System according to claim 2 wherein the medical device comprises an inlet movable element and an outlet movable element coupled to an inlet/outlet transponder element.

6. System according to claim 1 wherein the control device comprises a logic unit configured to discriminate which one or more of the movable elements are displaced based on the read out of the capacitance and/or the inductance and/or the resistance and/or the resonant frequency and/or the Q factor of the transponder circuit.

7. System according to claim 6 wherein the logic unit is configured to determine any one or more of the following conditions
substantially unchanged fluidic pressure during operation of the flow regulator indicating correct operation of the medical device,
decrease of fluidic pressure at the inlet side indicating exhaustion of fluid at the inlet side,
increase of fluidic pressure at the inlet side indicating excess of fluid at the inlet side,
increase of fluidic pressure at the outlet side indicating an occlusion at the outlet side,
operational status of the flow regulator,
passage of fluid in the fluidic conduit for the first time.

8. System according to claim 7 wherein the control device is configured to operate or to interrupt operation of the flow regulator in response to a determined condition, and/or to generate a user identifiable signal.

9. System according to claim 1 wherein the medical device further comprises a telemetric tag connected to the transponder circuit and wherein the transceiver is configured to transmit energy to the telemetric tag for measuring the capacitance and/or the inductance and/or the resistance and/or the resonant frequency and/or the Q factor of the transponder circuit and to read out the capacitance and/or the inductance and/or the resistance and/or the resonant frequency and/or the Q factor of the transponder circuit via the telemetric tag.

10. System according to claim 9 wherein the telemetric tag stores information related to the fluidic conduit such as the diameter and/or length of the fluidic conduit and/or related to the pump such as the specifications of the pump and/or related to the reservoir such as the reservoir capacity and/or type of medicament and the control device is configured to read said information via the transceiver and to operate the flow regulator based on said information.

11. Medical device according to claim 1 wherein the flow regulator is a pump for pumping the fluid or a valve or a flow restrictor for regulating the flow of the fluid.

12. System according to claim 1 wherein the flow regulator comprises a passive energy-receiving unit and wherein the control device comprises an energy-transfer unit for transferring operational energy to the energy-receiving unit for operating the flow regulator.

13. System according to claim 1 wherein the control device is configured to be temporarily placed in an energy-transfer position with respect to the medical device for operating the flow regulator and/or for transferring energy to the transponder circuit, wherein in the energy-transfer position the control device is separated from the medical device.

14. System according to claim 1 wherein the transponder circuit is integrated in a foil or plate like substrate arranged in the medical device such that a transponder element is coupled with a respective movable element.

15. System according to claim 1 wherein the movable elements are of different type or size and/or are displaceable to a different extent and/or arranged with respect to the transponder elements, and/or wherein the transponder elements are of different type or size and/or are arranged with respect to the movable elements, such that the capacitance and/or the inductance and/or the resistance and/or the resonant frequency and/or the Q factor of the transponder circuit is changed to a different extent or in an inverse manner when the movable elements are displaced.

16. The medical device of claim 1 further comprising a foil or plate-like substrate which comprises at least one transponder circuit.

* * * * *